United States Patent [19]

Nadaud et al.

[11] Patent Number: 5,605,694
[45] Date of Patent: Feb. 25, 1997

[54] STABILIZED EMULSION INTENDED TO MOISTURIZE THE SKIN, AND USE THEREOF

[75] Inventors: Jean-Francois Nadaud, Clamart; Jean-Pierre Laugier, Antony; Isabelle Le Royer, Jouy en Josas; Dominique Bernard, Paris, all of France

[73] Assignee: L'Oreal, Paris, France

[21] Appl. No.: 381,153

[22] Filed: Jan. 31, 1995

[30] Foreign Application Priority Data

Jan. 31, 1994 [FR] France ................................ 94 01030

[51] Int. Cl.$^6$ ............................................. A61K 7/48
[52] U.S. Cl. ........................... 424/401; 514/844; 514/845; 514/846; 514/941
[58] Field of Search .................. 424/401; 514/844–846, 514/941

[56] References Cited

U.S. PATENT DOCUMENTS

| | | |
|---|---|---|
| 4,370,319 | 1/1983 | Chapin et al. ........................... 424/184 |
| 4,803,067 | 2/1989 | Brunetta et al. .......................... 424/63 |
| 5,254,331 | 10/1993 | Mausner ................................. 424/401 |

FOREIGN PATENT DOCUMENTS 9319730  10/1993  WIPO.

OTHER PUBLICATIONS

JP 89/115588 (Abstract) 1989.
JP 83/129892 (Abstract) 1983.
JP 910042610 (Abstract) 1991.
Chemical Abstracts, vol. 119, No. 146379 & JP-A-05139949 1991.
Database WPI Week 9244, Derwent Publications Ltd., London, GB; AN 92-360690 & JP-A-04 261 111.
Chemical Abstracts, vol. 115, No. 141986 & JP-A-03063208 1991.

*Primary Examiner*—Jyothsna Venkat
*Attorney, Agent, or Firm*—Oblon, Spivak, McClelland, Maier & Neustadt, P.C.

[57] ABSTRACT

The invention relates to a stabilized, cosmetically and/or dermatologically acceptable emulsion intended to moisturize the skin. This emulsion contains a fatty phase, an aqueous phase, at least one emulsifying agent and at least one moisturizing agent. The aqueous phase contains at least one phosphated compound capable of releasing, via an enzymatic reaction when it is in contact with the skin, an active agent other than the moisturizing agent, which promotes moisturization of the skin, and the fatty phase contains at least one silicone-containing gum and/or one perfluoro oil. The emulsion according to the invention makes it possible to combat ageing of the skin, acne, pigmentation of the skin and/or hair loss.

10 Claims, No Drawings

STABILIZED EMULSION INTENDED TO MOISTURIZE THE SKIN, AND USE THEREOF

BACKGROUND OF THE INVENTION

1. Field of the Invention

The present invention relates to a stabilized, cosmetically and/or dermatologically acceptable emulsion intended to moisturize human facial and/or body skin, including the scalp and the nails. More precisely, it contains a fatty phase, an aqueous phase, at least one emulsifying agent and at least one moisturizing agent.

The invention also relates to a cosmetic use of this emulsion to combat ageing of the skin, acne, pigmentation of the skin and/or hair loss, and to a process for moisturizing the skin.

2. Discussion of the Background

The importance of keeping the skin well moisturized, both at the surface and in the deeper epidermal and dermal layers, is fully understood. It is also necessary to supply the skin with moisturizing active agents.

As the skin gets older, various signs of ageing appear on the skin, these being reflected especially in a modification of the cutaneous structure and function. This ageing is physiological in nature but is also photo-induced, that is to say that it is due to the repeated exposure of the skin to light and, consequently, to the formation of oxygenated free radicals by the action of this light on the constituents of the skin.

The main clinical signs of cutaneous ageing are particularly the following: appearance of deep wrinkles which increase with age. Disruption of the "grain" of the skin is observed in particular, that is the microrelief is less uniform and has an anisotropic nature.

Moreover, the complexion of the skin is generally modified; it appears paler and yellower, which appears to be due essentially to disturbance of the microcirculation (less haemoglobin in the dermal capillaries). Many colored blemishes appear at the skin surface, due to impaired melanogenesis. Diffuse irritations, and sometimes telangiectasia, occur in certain areas.

Another clinical sign of ageing is the dry and rough appearance of the skin which is essentially due to more considerable desquamation caused by diffracting light rays. These squama also contribute towards the somewhat grey appearance of the complexion.

Moreover, it is increasingly sought to introduce active agents, for instance vitamins such as vitamins A, B, C, D, E or F, into cosmetic and/or dermatological compositions in order to provide specific treatments against ageing of the skin, its drying, against acne and certain skin diseases (psoriasis), or to promote cicatrization of wounds and/or restructuring of the skin.

In particular, the presence of a sufficient amount of ascorbic acid or vitamin C, especially on the skin, enables stimulation of the growth of connective tissue, and especially that of collagen. Ascorbic acid also enables the cutaneous tissue defenses to be strengthened against external aggressions such as those of ultraviolet radiation, pollution, and drug, alcohol or tobacco aggressions.

However, a certain number of moisturizing reagents such as vitamin C are known to be unstable. For example, B. R. Hajratwala, "Stability of ascorbic acid", Sciences Pharmaceutiques Revue (Review of Pharmaceutical Sciences) pages 281–286, teaches that ascorbic acid possesses instability properties in aqueous, aerobic or anaerobic media, with a more pronounced instability in aerobic media.

Illustrations are given therein regarding the behavior of ascorbic acid in particular towards variations in pH of the solution containing it, variations in light, in temperature, and towards compounds such as surfactants, solvents and catalysts, particularly metal catalysts. Such behavior of ascorbic acid in aqueous media leads to the requirement for it to be stabilized. This has already been proposed in Patents JP 89/115,558 and JP 83/129,892, which teach, on the one hand, of blocking the reactive site of ascorbic acid, namely the hydroxyl site, by esterification and/or etherification especially with phosphated, sulphated or alkylated derivatives, and, on the other hand, of the use of these derivatives in cosmetic compositions in order to play the same role as that of vitamin C. This blocking of the active site thus enables ascorbic acid to be rendered more stable; it is, however, less effective than vitamin C in the free state (that is to say containing no additional groups).

Other modes of stabilizing ascorbic acid have been proposed, including esterification of an ascorbic acid derivative, and of a tocopherol derivative, with phosphoric acid (see for example, KAKUJI TOJO and AE-RIC LEE, "Bioconversion of a vitamin to vitamins C and E in skin", J. Cosmet. Chem., vol. 38, pages 333–339). However, the use of this type of diester in cosmetic compositions does not permit ascorbic acid to be released rapidly or in sufficient amounts at the skin surface.

Moreover, ascorbic acid and retinol are known to provoke skin irritations when they are used in cosmetic and/or dermatological compositions, in the free state and at high concentration.

Other active agents, such as nucleotides, are difficult to dissolve. Yet others, such as certain vitamins, are not readily bioavailable.

Moreover, a cosmetic bleaching composition containing a silicone oil, glycerine and magnesium ascorbyl phosphate is known from the document JP-A-05139949. This composition does not allow for good moisturization of the skin.

SUMMARY OF THE INVENTION

Accordingly, one object of the present invention is to provide a cosmetic and/or dermatological moisturizing emulsion which enables a sizeable amount of active agent to be released, with a good yield and from a precursor, via enzymatic hydrolysis, when the emulsion comes into contact with the *Stratum corneum*.

The Applicant has discovered, surprisingly, this and other objects can be achieved by an emulsion containing in the aqueous phase, a phosphated compound capable of releasing, via an enzymatic reaction when it comes into contact with the skin, an active agent other than the moisturizing agent, which promotes moisturization of the skin, and in the fatty phase, at least one silicone-containing gum and/or one perfluoro oil, which enables the skin to be moisturized effectively, while also ensuring a good yield for the enzymatic hydrolysis of the active agent precursor.

DETAILED DESCRIPTION OF THE PREFERRED EMBODIMENTS

The presence in the emulsion according to the invention of a silicone-containing and/or fluoro oil allows the yield for the enzymatic hydrolysis to be enhanced when the emulsion is applied to the skin, and thus its moisturizing role to be enhanced.

Cutaneous acid phosphatase possesses a good kinetic yield for the hydrolysis of phosphated active agent precursors, such as magnesium ascorbyl phosphate, in a medium having a temperature of about 30° C. and a relative humidity of about 90%.

Thus, in order to be within the optimum temperature and humidity conditions of the *Stratum corneum* and close to those required for a good yield in the enzymatic hydrolysis, it is necessary to combine specific moisturizing agents and surfactants or emulsifying agents with the phosphated active agent.

The emulsion according to the invention gives good results, regardless of the skin type to which it is applied.

According to the invention, one or more phosphated compounds may be chosen, these being chosen from vitamin phosphates, nucleotides, phosphated hydroxyacetones, glycerophosphates (disodium betaglycerol phosphate tetrahydrate) and mixtures thereof.

Among the vitamin phosphates, ascorbic acid phosphates, tocopherol phosphates, retinol phosphates, vitamin D phosphates, vitamin B phosphates and vitamin F phosphates (also known as essential fatty acid phosphates) may be used. Among the nucleotides, adenosine phosphate, guanosine phosphate, cytosine phosphate, uridine phosphate, thymidine phosphate, inosine phosphate and xanthosine phosphate may be used.

The phosphated compound used in the emulsion according to the invention is preferably an ascorbic acid phosphate and more specifically the ascorbyl phosphate of an alkali metal or alkaline-earth metal such as magnesium, potassium, sodium or lithium.

The perfluoro oil is, for example, a perfluoropolyether such as perfluoropolymethyl isopropyl ether, or a perfluoroalkane.

The silicone-containing gum of considerable molecular weight is, for example, a dimethiconol (or polydimethylsiloxanol), such as the silicone gum sold under the trade name "QC F2-1671" by Dow Corning.

The emulsion according to the invention may also contain a silicone-containing oil. This oil may be chosen from volatile or non-volatile, cyclic or acyclic silicone-containing oils, such as penta- or hexadimethylsiloxane, or polydimethylsiloxanes with a viscosity of not more than 0.06 m²/s.

The emulsion according to the invention may also contain a plant oil chosen from the liquid fractions of karite butter (or shea butter, see U.S. Pat. No. 4,661,343), apricot oil, blackcurrant seed oil, jojoba oil, sesame oil, macadamia oil, sunflower oil, and muscat rose oil.

The emulsifying agents which may be used in the invention are preferably nonionic surfactants, which preserve the enzymatic activity involved. These nonionic surfactants are particularly chosen from oxyethylenated surfactants of general formula:

$$R^1-(O-CH_2-R^2)_n-OH$$

where n is an integer ranging from 1 to 100; n is preferably 1, 9, 23 or 100.

$R^1$ is a linear or branched alkyl radicals having from 8 to 30 carbon atoms, linear or branched alkene radicals having from 8 to 30 carbon atoms, a hydrogen atom, an aryl group having 6 to 12 carbon atoms which is optionally substituted with an alkyl radical, $R^3$, having from 1 to 12 carbon atoms, a heterocyclic group having 6–20 carbon atoms of which any carbon atom may be replaced with an oxygen, nitrogen or sulfur atom, or a group of the formula

where $R^4$ is an alkyl group having from 8 to 22 carbon atoms. $R^1$ is preferably chosen from hydrogen, a $C_{12}$ alkyl radical, a phenyl group which is substituted with a $C_8$ alkyl radical, or the group

where $R^4$ is $C_{11}$ to $C_{17}$ alkyl.

$R^2$ is a linear or branched alkyl radicals having from 1 to 30 carbon atoms, linear or branched alkene radicals having from 1 to 30 carbon atoms, which are optionally hydroxylated. $R^2$ is preferably —$CH_2$— or a radical of the formula

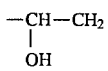

The oxyethylenated surfactants used according to the invention have from 1 to 30 mol of ethylene oxide and preferably 8 to 12 mol of ethylene oxide.

These oxyethylenated surfactants are more especially obtained by reaction between a polyhydric alcohol (glycerol, oxyethylenated sorbitan, polyethylene glycol) and a $C_{12}$ to $C_{22}$ fatty acid (stearic acid, oleic acid, lauric acid), or from oxyethylenated alcohols (lauryl alcohol containing 23 mol of ethylene oxide, octylphenyl containing 9 mol of ethylene oxide, polyglycerolated dodecanediol containing 3.5 mol of ethylene oxide, and polyethylene glycol containing 6 mol of ethylene oxide).

The emulsifying agents may also be saccharide esters.

Among the saccharide esters, there may especially be used $C_3$ to $C_6$ saccharide esters, optionally containing a $C_1$ to $C_{30}$ carbon chain. Suitable saccharide esters include dodecylmaltoside, methylglucose dioleate, and polyoxyethylenated sorbitan monooleate containing 20 mol of ethylene oxide.

The moisturizing agent or agents are used in the emulsion according to the invention so as to preserve the activity of cutaneous acid phosphatase and to enhance the yield for the activity thereof. Suitable moistening agents include those which are conventionally used in the cosmetics and/or dermatological fields. These moisturizing agents include propylene glycol, polyoxyethylenated polyhydric alcohols, vaseline, mineral oils, sodium pyroglutamate, hyaluronic acid, chitosan derivatives, lactamide, acetamide, thiamorpholinone, alphahydroxylated carboxylic acids having from 3 to 20 carbon atoms, polyols (glycerol, sorbitol, D-panthenol, diglycerol, mannitol, inositol, aminopolyol), polysaccharides, proteins such as collagen, polyol saccharides such as alginates, and lipoproteins.

The emulsion according to the invention may also contain cosmetically and/or dermatologically acceptable adjuvants such as gelling and thickening agents (carboxyvinyl polymers, glyceryl poly(meth)acrylates, polyacrylamides) other than a silicone gum, fragrances, fillers (talc), preserving agents, simple electrolytes (NaCl, NaOH, KCl), and coemulsifying agents.

In order to enhance the stability of the emulsion, one or more stabilizing agents may also be added, such as a mixture of titanium dioxide and starch powder.

The emulsion according to the invention may be provided in the form of an oil-in-water (OIW) emulsion or a water-in-oil (W/O) emulsion, optionally containing spherules (liposomes, nanocapoules or nanospheres) into which the moisturizing agents and/or other active agents may be introduced.

The proportion of the fatty phase is within a range of from 5% to 25% by weight, and preferably of from 6% to 12% by weight, relative to the total weight of the emulsion.

In practice, the moisturizing agent is chosen in a range of from 0.1% to 20% by weight, and preferably of from 1% to 10% by weight, relative to the total weight of the emulsion.

The emulsifying agent is chosen in particular in a range of from 0.1% to 10% by weight, and preferably of from 0.1% to 3% by weight, relative to the total weight of the composition.

The phosphated compound is preferably in a range of from 0.01% to 10% by weight, and preferably of from 0.01% to 1% by weight, relative to the total weight of the composition.

The adjuvants are separately within a range of from 0.05% to 2% by weight, and preferably within a range of from 0.05% to 0.5% by weight, relative to the total weight of the emulsion.

The oily phase of the emulsion preferably contains 1/6 of perfluoro oil, 1/6 of plant oil and 2/3 of silicone oil.

The emulsion according to the invention also relates to a cosmetic and/or dermatological composition for combating ageing of the skin, acne, pigmentation of the skin and/or hair loss, and to a use of the emulsion defined above for combating these consequences of dehydration.

This invention also relates to a process for moisturizing the skin, which consists in applying to the skin the emulsion according to the invention.

This application is based on French application 94-01030, filed Jan. 31, 1994; the text of which is incorporated in its entirety herein by reference.

EXAMPLES

Having generally described this invention, a further understanding can be obtained by reference to certain specific examples which are provided herein for purposes of illustration only and are not intended to be limiting unless otherwise specified. The amounts are given as percentages by weight.

Example 1: W/O Emulsion

| Oily phase: | |
| --- | --- |
| Liquid fraction of karite butter | 1 |
| Polymethylisopropyl perfluoro ether (MW 3200) | 1 |
| Cyclopentadimethylsiloxane | 8 |
| Polydimethylsiloxanol (silicone gum) | 0.1 |
| Glyceryl monostearate (emulsifying agent) | 1.5 |
| Catyl alcohol (co-emulsifying agent) | 0.25 |
| Aqueous Phase: | |
| Magnesium ascorbyl phosphate (moisturizing agent) | 0.2 |
| Carboxyvinyl polymer (gelling agent) | 0.35 |
| Tetrahydrated disodic beta-glycerol phosphate (phosphated compound) | 0.1 |
| Sodium hydroxide (neutralizing) | 0.2 |
| Propylene glycol (moisturizing agent) | 3 |
| Fragrance | 0.2 |
| Preserving agents | 0.3 |
| Water   qs | 100 |

This emulsion affords a white cream, for moisturizing facial skin.

Example 2: O/W Emulsion

| Oily phase: | |
| --- | --- |
| Isopropyl myristate (oil) | 2 |
| Cyclopentadimethylsiloxane | 5 |
| Polydimethylsiloxanol (silicone gum) | 0.25 |
| PEG-100 stearate (emulsifying agent) | 2 |
| Stearic acid | 0.6 |
| Aqueous phase: | |
| Polyethylene glycol 400 | 3 |
| Propylene glycol | 2 |
| Hyaluronic acid (moisturizing agent) | 0.1 |
| Magnesium ascorbyl phosphate (moisturizing agent) | 0.25 |
| Sodium hydroxide (neutralizing agent) | 0.15 |
| Carboxyvinyl polymer (gelling agent) | 0.2 |
| Fragrance | 0.3 |
| Preserving agent | 0.3 |
| Water   qs | 100 |

This emulsion affords a white cream, for moisturizing the skin of the human body.

Example 3: O/W Emulsion

| Oily Phase: | |
| --- | --- |
| Cyclopentadimethylsiloxane | 85 |
| Polydimethylsiloxanol (silicone gum) | 0.5 |
| Polymethylisopropyl perfluoro ether (perfluoro oil) | 1 |
| PEG-100 stearate/glyceryl stearate (emulsifying agent) | 0.3 |
| Stearic acid | 0.6 |
| Cetyl alcohol | 0.5 |
| Aqueous phase: | |
| Magnesium ascorbyl phosphate (moisturizing agent) | 0.25 |
| Carboxyvinyl polymer (gelling agent) | 0.1 |
| Sodium hydroxide (neutralizing agent) | 0.18 |
| Polyglyceryl methacrylate (gelling agent) | 8 |
| Polyacrylamide | 0.1 |
| Panthenol (moisturizing agent) | 1 |
| Fragrance | 0.2 |
| Preserving agent | 0.6 |
| Water   qs | 100 |

This emulsion affords a white cream intended to moisturize the face.

A moisturization test was performed with the cream of Example 3 (cream A) compared with a cream having an identical composition but containing no silicone gum or perfluoro oil (cream B).

This test consisted in measuring, using a Dermodiag (measurement of the impedance) and using an Infraanalyzer 450 (measurement of the water peak by infra-red), the moisturization of the skin after the creams have been applied to the inner face of the forearm of the 15 subjects on the test panel.

In a first step, the measurements were made 5 h (Infraanalyzer) and 24 h (Dermodiag) after is treatment. The percentage increase in moisturization was determined. The results are as follows:

| Time | Cream A | Cream B |
| --- | --- | --- |
| 5 h (Infraanalyzer) | +2.3% | +1.7% |
| 24 h (Dermodiag) | +11% | +8% |

These results show that both creams moisturize, but that the moisturization is more prolonged with the cream according to the invention. A significant moisturizing superiority with the cream according to the invention is thus apparent from the comparison.

A long-term test was also performed, consisting in measuring, with a Dermodiag (measurement of the impedance), the moisturization of the skin after application of the creams to the inner face of the forearm of the 15 subjects on the test panel for 18 consecutive days.

The measurements were made on day 18, i.e. at the termination of the treatment, and on day 24, i.e. three days after termination of the treatment.

| Time | Cream A | Cream B |
| --- | --- | --- |
| 18 days | +18% | +11% |
| 24 days | +9% | +8% |

A superiority of the cream according to the invention after treatment for 18 days is apparent from the comparison between the two products.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A stabilized, cosmetically or dermatologically acceptable moisturizing emulsion comprising 6 to 12% by weight, relative to the total weight of the emulsion, of a fatty phase comprising a mixture of polydimethylsiloxane and polymethylisopropyl perfluoro ether, an aqueous phase comprising 0.01 to 1% by weight, relative to the total weight of the emulsion, of an ascorbyl phosphate alkaline earth metal or alkali metal salt, 0.1 to 10% by weight, relative to the total weight of the emulsion, of at least one emulsifying agent, and 0.1 to 20% by weight, relative to the total weight of the emulsion, of at least one moisturizing agent.

2. The emulsion according to claim 1, which further comprises a plant oil.

3. The emulsion according to claim 1, wherein said emulsifying agent is an oxyethylenated nonionic surfactant or a saccharide ester.

4. The emulsion according to claim 3, wherein said emulsifying agent is an oxyethylenated fatty alcohol having from 1 to 30 mol of ethylene oxide.

5. The emulsion according to claim 1, wherein said moisturizing agent is a polyol.

6. The emulsion according to claim 5, wherein said moisturizing agent is glycerol.

7. The emulsion according to claim 1, which further comprises an adjuvant selected from the group consisting of preserving agents, fragrances, fillers, gelling and thickening agents other than a silicone gum, simple electrolytes and co-emulsifying agents.

8. A method of treating skin to combat aging of the skin, acne, pigmentation of the skin, hair loss or drying of the skin, comprising applying a cosmetically or dermatologically acceptable moisturizing emulsion comprising 6 to 12% by weight, relative to the total weight of the emulsion, of a fatty phase comprising a mixture of polydimethylsiloxane and polymethylisopropyl perfluoro ether, an aqueous phase comprising 0.01 to 1% by weight, relative to the total weight of the emulsion, of an ascorbyl phosphate alkaline earth metal or alkali metal salt, 0.1 to 10% by weight, relative to the total weight of the emulsion, of at least one emulsifying agent, and 0.1 to 20% by weight, relative to the total weight of the emulsion, of at least one moisturizing agent.

9. A process for moisturizing skin which comprises applying to skin a cosmetically or dermatologically acceptable moisturizing emulsion comprising 6 to 12% by weight, relative to the total weight of the emulsion, of a fatty phase comprising a mixture of polydimethylsiloxane and polymethylisopropyl perfluoro ether, an aqueous phase comprising 0.01 to 1% by weight, relative to the total weight of the emulsion, of an ascorbyl phosphate alkaline earth metal or alkali metal salt, 0.1 to 10% by weight, relative to the total weight of the emulsion, of at least one emulsifying agent, and 0.1 to 20% by weight, relative to the total weight of the emulsion, of at least one moisturizing agent.

10. A cosmetic or dermatological composition for combating aging of the skin, acne, pigmentation of the skin or hair loss, comprising a carrier and a cosmetically or dermatologically acceptable moisturizing emulsion comprising 6 to 12% by weight, relative to the total weight of the emulsion, of a fatty phase comprising a mixture of polydimethylsiloxane and polymethylisopropyl perfluoro ether, an aqueous phase comprising 0.01 to 1% by weight, relative to the total weight of the emulsion, of an ascorbyl phosphate alkaline earth metal or alkali metal salt, 0.1 to 10% by weight, relative to the total weight of the emulsion, of at least one emulsifying agent, and 0.1 to 20% by weight, relative to the total weight of the emulsion, of at least one moisturizing agent.

* * * * *